United States Patent
Tsuge et al.

(10) Patent No.: US 12,151,069 B2
(45) Date of Patent: Nov. 26, 2024

(54) GUIDE WIRE

(71) Applicant: ASAHI INTECC CO., LTD., Aichi (JP)

(72) Inventors: Kenta Tsuge, Seto (JP); Tomoki Ichikawa, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 573 days.

(21) Appl. No.: 16/846,450

(22) Filed: Apr. 13, 2020

(65) Prior Publication Data
US 2020/0238055 A1 Jul. 30, 2020

Related U.S. Application Data

(63) Continuation of application No. PCT/JP2017/037000, filed on Oct. 12, 2017.

(51) Int. Cl.
*A61M 25/09* (2006.01)

(52) U.S. Cl.
CPC ... *A61M 25/09* (2013.01); *A61M 2025/09083* (2013.01); *A61M 2025/09166* (2013.01)

(58) Field of Classification Search
CPC ......... A61M 2025/09083; A61M 2025/09166; A61M 2025/09141; A61M 2025/09158;
(Continued)

(56) References Cited

U.S. PATENT DOCUMENTS 3,217,705 A * 11/1965 Billings ............ A61M 25/0108
600/431
5,144,959 A * 9/1992 Gambale ............... A61M 25/09
604/170.01
(Continued)

FOREIGN PATENT DOCUMENTS

| CN | 103830830 A | 6/2014 |
|---|---|---|
| EP | 2 732 846 A1 | 5/2014 |

(Continued)

OTHER PUBLICATIONS

Office Action issued Apr. 11, 2022, in related U.S. Appl. No. 16/846,446.
(Continued)

*Primary Examiner* — Benjamin S Melhus
*Assistant Examiner* — Samuel C Kim
(74) *Attorney, Agent, or Firm* — XSENSUS LLP

(57) ABSTRACT

A guide wire includes a core shaft having a distal end portion stepwisely decreasing in diameter, an inner coil body covering at least a part of an outer periphery of the distal end portion, an outer coil body covering an outer periphery of the inner coil body, and a distal end fixing portion that fixes distal ends of the core shaft. The distal end portion includes a small diameter portion, a large diameter portion inside the inner coil body and the outer coil body further in the proximal end direction than the small diameter portion and having a larger diameter than that of the small diameter portion, and a tapered portion that increases in diameter from the small diameter portion toward the large diameter portion. A radiopaque marker is on an outer peripheral surface of the tapered portion. A gap is between the radiopaque marker and the inner coil body.

17 Claims, 4 Drawing Sheets

(58) Field of Classification Search
CPC .............................. A61M 2025/0233; A61M 2025/09008–09191; A61M 25/09–0905; A61F 2/00; A61F 2400/16; A61F 2002/3006; A61F 2002/30092
See application file for complete search history.

(56) References Cited

U.S. PATENT DOCUMENTS

| | | | | |
|---|---|---|---|---|
| 5,267,574 | A * | 12/1993 | Viera | A61M 25/09 604/528 |
| 6,093,157 | A * | 7/2000 | Chandrasekaran | A61B 17/320758 600/585 |
| 6,612,998 | B2 * | 9/2003 | Gosiengfiao | A61M 25/09 600/585 |
| 7,455,646 | B2 * | 11/2008 | Richardson | A61M 25/09 600/585 |
| 2003/0069521 | A1 * | 4/2003 | Reynolds | A61M 25/09 600/585 |
| 2003/0100848 | A1 | 5/2003 | Gosiengfiao et al. | |
| 2004/0106878 | A1 | 6/2004 | Skujins et al. | |
| 2004/0167440 | A1 * | 8/2004 | Sharrow | A61M 25/09 600/585 |
| 2007/0112282 | A1 | 5/2007 | Skujins et al. | |
| 2007/0282225 | A1 * | 12/2007 | Terashi | A61M 25/09 600/585 |
| 2008/0262474 | A1 | 10/2008 | Northrop | |
| 2009/0227900 | A1 * | 9/2009 | Kim | A61M 25/09 600/585 |
| 2011/0208092 | A1 * | 8/2011 | Nishigishi | A61M 25/09 600/585 |
| 2014/0142557 | A1 | 5/2014 | Kosugi et al. | |
| 2014/0350519 | A1 | 11/2014 | Urie | |
| 2015/0148706 | A1 | 5/2015 | Abner | |
| 2016/0346518 | A1 | 12/2016 | Terashi et al. | |
| 2020/0237355 | A1 | 7/2020 | Tsuge et al. | |

FOREIGN PATENT DOCUMENTS

| | | | |
|---|---|---|---|
| JP | 6-54912 A | 3/1994 | |
| JP | 7-80076 A | 3/1995 | |
| JP | 2010-524588 A | 7/2010 | |
| JP | 2011-000469 A | 1/2011 | |
| JP | 2016-221198 A | 12/2016 | |
| JP | 2017-500925 A | 1/2017 | |
| WO | WO-8707493 A1 * | 12/1987 | ............ A61B 6/00 |
| WO | WO-2005030311 A1 * | 4/2005 | ............ A61M 25/09 |
| WO | 2010/108308 A1 | 9/2010 | |
| WO | 2015/080948 A1 | 6/2015 | |

OTHER PUBLICATIONS

International Search Report and Written Opinion mailed on Nov. 28, 2017 for PCT/JP2017/037000 filed on Oct. 12, 2017, 8 pages including English Translation of the International Search Report.

\* cited by examiner

GUIDE WIRE

CROSS REFERENCE TO RELATED APPLICATION

This application is a continuation application of International Application No. PCT/JP2017/037000, filed Oct. 12, 2017. The contents of these applications are incorporated herein by reference in their entirety.

TECHNICAL FIELD

The present disclosure relates to a guide wire.

BACKGROUND

When treating a stenosis that occurs in blood vessels such as coronary arteries surrounding the heart, or when treating a region where the blood vessel is completely occluded due to the progress of calcification (for example, chronic total occlusion: CTO), a guide wire for guiding a treatment instrument such as a balloon catheter is inserted into the blood vessel, prior to the treatment instrument.

The above-described guide wire is required to be able to advance in a delicate and intricately curved blood vessel such as a coronary artery for smooth introduction into a deep part of the blood vessel. For example, there has been proposed a guide wire that includes a core shaft having flexibility provided by a tapered portion of the distal end portion stepwisely thinner toward the distal end side and a metal coil wound multiple times around the outside of the core shaft, in which the proximal end of each coil is brazed to the core shaft, according to JP H07-80076.

Such a guide wire provides excellent flexibility of the distal end portion that allows the guide wire to easily follow the above-described blood vessel. Further, the rotational force can be securely transmitted to the distal end portion of the guide wire so that an appropriate course can be selected.

SUMMARY

However, in a case where the conventional guide wire as described above is used, stress is concentrated on the tapered portion when the guide wire is bent. This stress may cause breakage of the core shaft or elongation of wires of the coil body, thereby deteriorating restorability.

Embodiments have been made on the basis of the above-described circumstances, and aims at providing a guide wire capable of preventing breakage of the core shaft and deterioration of restorability due to elongated wires of the coil body when the guide wire is bent and other problems.

A guide wire according to an embodiment of the present disclosure includes a core shaft that includes a distal end portion stepwisely decreasing in diameter toward a distal end direction, an inner coil body that is wound to cover at least a part of an outer periphery of the distal end portion having a decreased diameter, an outer coil body that is wound to cover at least an outer periphery of the inner coil body, and a distal end fixing portion that fixes the distal end of the core shaft, a distal end of the inner coil body, and a distal end of the outer coil body to one another. The distal end portion of the core shaft includes a small diameter portion adjacent to the distal end fixing portion, a large diameter portion inside the inner coil body and the outer coil body further in a proximal end direction than the small diameter portion and has a larger outer diameter than a diameter of the small diameter portion, and a tapered portion between the small diameter portion and the large diameter portion. The tapered portion is continuous with the small diameter portion and the large diameter portion and increases in diameter from the small diameter portion toward the large diameter portion. A radiopaque marker is on an outer peripheral surface of the tapered portion. A gap is between the radiopaque marker and the inner coil body.

DETAILED DESCRIPTION

Figure 1:
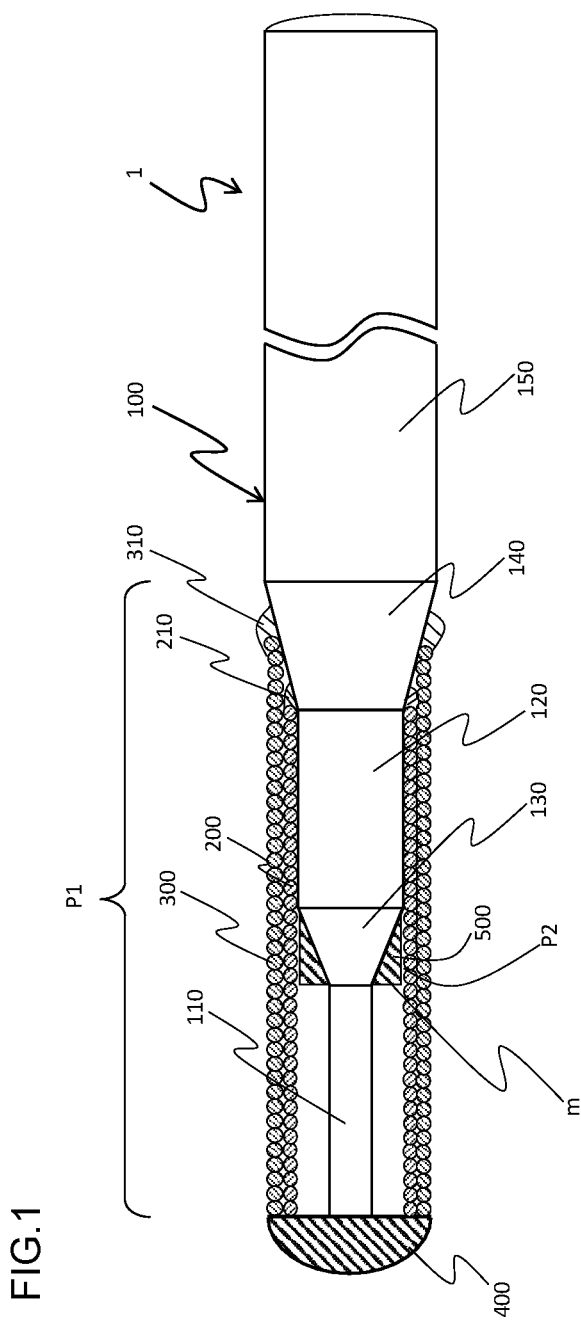
FIG. 1 is a schematic section view illustrating an embodiment of the disclosure.

As used herein, an element or step recited in the singular and proceeded with the word "a" or "an" should be understood as not excluding plural elements, unless such exclusion is explicitly recited. Furthermore, references to "one embodiment" of the present invention are not intended to be interpreted as excluding the existence of additional embodiments that also incorporate the recited features.

Note that in the specification, "distal end direction" is a direction along the axial direction of the guide wire and indicates a direction of the side on which the distal end fixing portion is positioned relative to the large diameter portion of the core shaft. The "proximal end direction" is a direction along the axial direction of the guide wire and indicates the direction opposite to the distal end direction.

A guide wire of the disclosure includes a core shaft that includes a distal end portion stepwisely decreasing in diameter toward a distal end direction, an inner coil body that is wound to cover at least a part of an outer periphery of the distal end portion decreased in diameter, an outer coil body that is wound to cover at least an outer periphery of the inner coil body, and a distal end fixing portion that fixes the distal end of the core shaft, a distal end of the inner coil body, and a distal end of the outer coil body to one another. The distal end portion of the core shaft includes a small diameter portion that is adjacent to the distal end fixing portion, a large diameter portion inside the inner coil body and the outer coil body further in a proximal end direction than the small diameter portion and has a larger diameter than the small diameter portion, and a tapered portion between the small diameter portion and the large diameter portion. The tapered portion is continuous between the small diameter portion and the large diameter portion and increases in diameter from the small diameter portion toward the large diameter portion. A radiopaque marker is on an outer peripheral surface of the tapered portion. A gap is between the radiopaque marker and the inner coil body.

Hereinafter, embodiments of the present disclosure will be described with reference to drawings. However, embodiments are not limited only to those illustrated in the drawings.

FIG. 1 is a schematic section view illustrating an embodiment of the disclosure. As illustrated in FIG. 1, the guide wire 1 roughly includes a core shaft 100, an inner coil body 200, an outer coil body 300, a distal end fixing part 400, and a marker part 500.

The core shaft 100 has a distal end portion PI stepwisely reducing in diameter toward a distal end direction. The distal end portion PI of the core shaft 100 includes a small diameter portion 110 that is continuous with the distal end fixing portion 400, a large diameter portion 120 that is located inside the inner coil body 200 and the outer coil body 300 further in a proximal end direction than the small diameter portion 110 and has a larger outer diameter than an outer diameter of the small diameter portion 110, and a tapered portion 130 that is continuous with the small diameter portion 110 and the large diameter portion 120 and increases in diameter from the small diameter portion 110 toward the large diameter portion 120. Note that the distal end fixing part 400, the inner coil body 200, and the outer coil body 300 will be described later.

The core shaft 100 includes the cylindrical small diameter portion 110 having the distal end continuous with the distal end fixing portion 400, i.e., is adjacent to the distal end fixing portion 400, and extending toward the proximal end direction, the tapered portion 130 having the distal end continuous with the small diameter portion 110 and extending toward the proximal end direction with the outer periphery gradually increasing in diameter, and the cylindrical large diameter portion 120 having the distal end continuous with the tapered portion 130 and extending toward the proximal end direction. In the embodiment, the proximal end of the large diameter portion 120 is connected to a core shaft main body 150 through a connection portion 140 having a truncated cone shape, e.g., tapered continuously with the large diameter portion 120 and the core shaft main body 150 and increases in diameter from the large diameter portion 120 toward the core shaft main body 150. Note that the rotation operation or the like of the guide wire 1 by a user are performed in the edge part in the proximal end direction of the core shaft main body 150.

The total length of the core shaft 100 may be 1,800 to 3,000 mm, e.g., 1,900 to 2,500 mm. The axial length of the distal end portion P1 of the core shaft 100 may be 200 to 1,000 mm, e.g., 300 to 850 mm. The outer diameter of the core shaft 100 may be 0.25 to 0.5 mm for the core shaft main body 150, ⅕ to ⅖ of the core shaft main body 150 for the large diameter portion 120, and ¹⁄₁₅ to ⅕ of the core shaft main body 150 for the small diameter portion 110. In the embodiment, the entire length is 1,900 mm, the axial length of the distal end portion P1 is 350 mm (the axial length of the small diameter portion 110 is 10 mm, the axial length of the tapered portion 130 is 5 mm, the axial length of the large diameter portion 120 is 250 mm, the axial length of the connection portion 140 is 85 mm), the outer diameter of the core shaft main body 150 is 0.35 mm, the outer diameter of the large diameter portion 120 is 0.14 mm, and the outer diameter of the small diameter portion 110 is 0.04 mm, as an example.

The material forming the core shaft 100 is not particularly limited as long as the flexibility of the small diameter portion 110 is secured and the material has antithrombogenicity and biocompatibility. For example, the material forming the core shaft 100 may include stainless steel, e.g., SUS304, a superelastic alloy such as a Ni-Ti alloy, or the like.

The inner coil body 200 is wound so as to cover at least a part of the outer periphery of the distal end portion P1 that is reduced in diameter relative to the core shaft main body 150. In the embodiment, the inner coil body 200 is spirally wound using one single wire so that the wires of the adjacent inner coil bodies 200 are in contact with each other, and the inner periphery of the inner coil body 200 is in close contact with the outer periphery of the large diameter portion 120 to cover the outer periphery of the large diameter portion 120. Moreover, the distal end of the inner coil body 200 is fixed to the distal end fixing part 400. Further, the proximal end of the inner coil body 200 is joined to the core shaft 100 with a brazing material 210 at the connection portion 140.

The outer coil body 300 is wound to cover at least the outer periphery of the inner coil body 200. In the embodiment, the outer coil body 300 is spirally wound using one single wire so that the wires of the adjacent outer coil bodies 300 are in contact with each other, and the inner periphery of the outer coil body 300 is in close contact with the outer periphery of the inner coil body 200 to cover the outer periphery of the inner coil body 200. Moreover, the distal end of the outer coil body 300 is fixed to the distal end fixing part 400. The outer coil body 300 may extend further from the distal end fixing portion 400 than the inner coil body 200. Further, the proximal end of the outer coil body 300 may be joined to the core shaft 100 with a brazing material 310 at the connection portion 140.

The diameter of the wires forming the inner coil body 200 and the outer coil body 300 may be 0.01 to 0.05 mm, e.g., 0.01 to 0.02 mm. In the embodiment, both the inner coil body 200 and the outer coil body 300 have a diameter of 0.015 mm, as an example.

The material forming the inner coil body 200 and the outer coil body 300 is not particularly limited as long as the flexibility of the small diameter portion 110 is secured and the material has antithrombogenicity and biocompatibility. For example, the material forming the inner coil body 200 and the outer coil body 300 may include stainless steel, e.g., SUS316, a superelastic alloy such as a Ni—Ti alloy, or the like.

Examples of the brazing material 210 and the brazing material 310 include metals, e.g., an Sn—Pb alloy, a Pb—Ag alloy, an Sn—Ag alloy, an Au—Sn alloy, or the like.

The distal end fixing portion 400 is a region where the distal end of the core shaft 100, the distal end of the inner coil body 200, and the distal end of the outer coil body 300 are fixed to one another. The distal end fixing portion 400 integrally connects the core shaft 100, the inner coil body 200, and the outer coil body 300, and the distal end thereof is formed, e.g., in a substantially hemispherical shape to prevent the guide wire 1 from damaging the inner wall of the blood vessel when advancing in the blood vessel. The distal end fixing portion 400 may be formed by brazing using metals, e.g., an Sn—Pb alloy, a Pb—Ag alloy, an Sn—Ag alloy, an Au—Sn alloy, or the like.

The marker part 500 includes a radiopaque substance m and may cover the entire outer peripheral surface of the tapered portion 130. Examples of the above-described radiopaque substance m include gold, platinum, tungsten, alloys containing these elements (e.g., platinum-nickel alloys), or the like. Note that the radiopaque substance m may be used in combination with another material such as a mixture with a non-radiopaque material or the radiopaque substance coated on a surface of a non-radiopaque material. The marker part 500 may have a tapered shape complementary to that of the tapered portion 130, such that an outer surface of the marker part 500 may be substantially flat.

Here, the marker part 500 has a gap P2 between the marker part 500 and the above-described inner coil body 200. That is, the marker part 500 and the inner coil body 200 are not fixed to or in contact with each other, and are arranged so as to be separated from each other. The gap P2 between the marker part 500 and the inner coil body 200 may be constant.

Next, the use mode of the guide wire 1 will be described. The guide wire 1 is inserted into a blood vessel of a body, e.g., in a thigh, from the distal end portion P1 and is advanced along the blood vessel towards a treatment region, e.g., towards a coronary artery. Next, after the guide wire 1 is advanced to pass the treatment region, e.g., a stenosis of a blood vessel or a false cavity near a CTO, a treatment instrument, e.g., a balloon catheter, a stent, or the like, is transported along the guide wire 1, so that various treatments are performed at the treatment region. After the treatment is completed, the guide wire 1 is withdrawn from the body by retrograding through the blood vessel, and a series of operations is completed.

Figure 3:
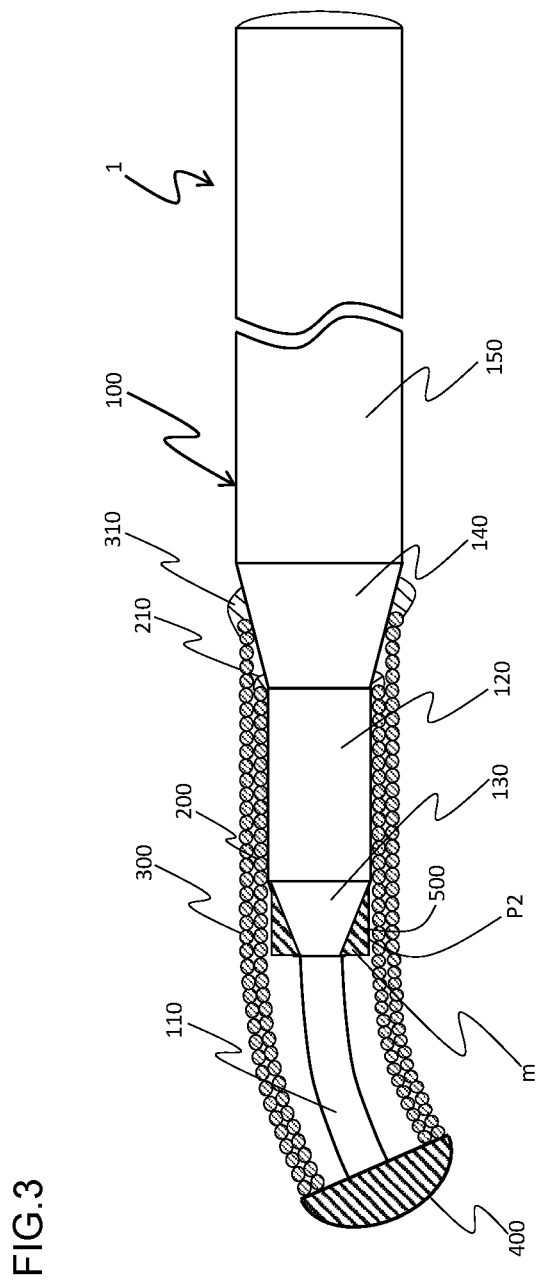
FIG. 3 is a schematic section view illustrating an example of a use state of the guide wire in FIG. 1.

Here, in the guide wire 1, the diameter of the distal end portion P1 is stepwisely reduced toward the distal end direction, which allows the small diameter portion 110 to be bent more easily than the core shaft main body 150 and the large diameter portion 120. In addition, with a gap P2 between the marker 500 and the inner coil body 200, the marker part 500 and the inner coil body 200 can freely move relative to each other along the axial direction of the core shaft 100. For this reason, when the guide wire 1 advances in the curved blood vessel, the small diameter portion 110 is bent (see FIG. 3) or restored easily with respect to the large diameter portion 120, allowing the guide wire 1 to advance smoothly in the blood vessel in accordance with the degree of curvature of the blood vessel.

Figure 2:
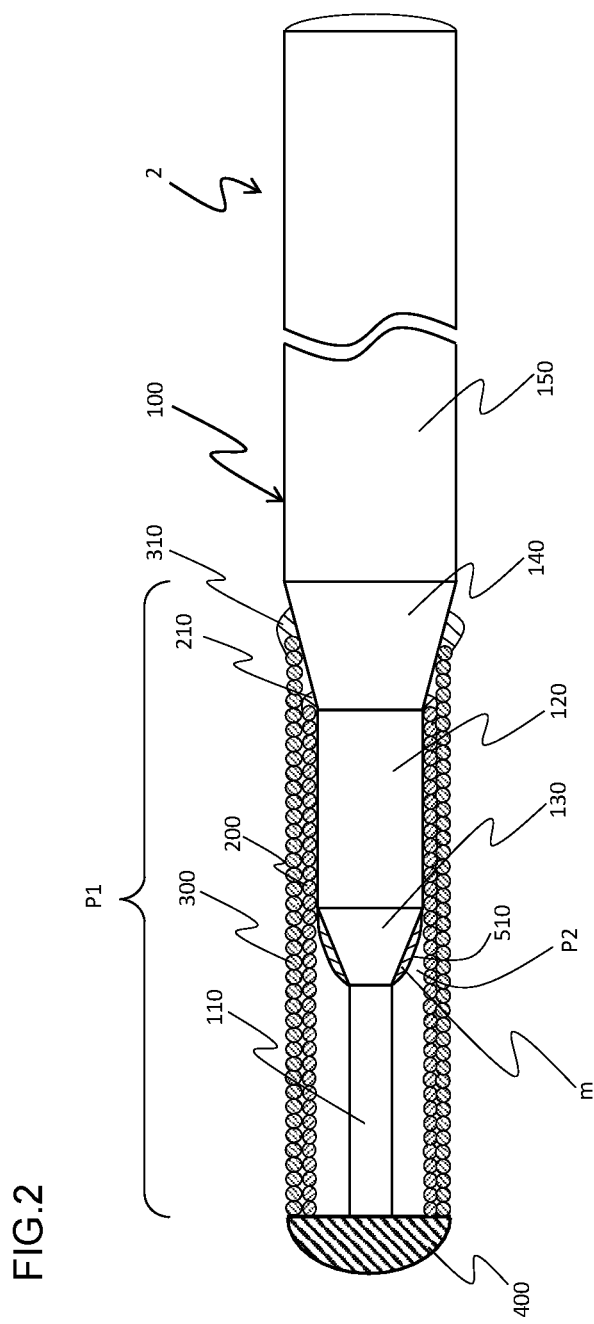
FIG. 2 is a schematic section view illustrating a modification of FIG. 1.

FIG. 2 is a schematic section view illustrating an embodiment of the disclosure. As illustrated in FIG. 2, the guide wire 2 roughly includes the core shaft 100, the inner coil body 200, the outer coil body 300, the distal end fixing part 400, and a marker part 510. In the guide wire 2, the gap P2 between the inner coil body 200 and the marker part 510 increases toward the distal end direction in a state where the core shaft 100 extends substantially in a straight line. To be more specific, in the guide wire 2, a distance between the outer periphery of the marker part 510 and the inner periphery of the inner coil body 200 in the radial direction of the core shaft 100 is gradually increased toward the distal end direction from the proximal end to the distal end of the marker part 510 in a state where the core shaft 100 extends substantially in a straight line (a state where the core shaft 100 is not bent). In other words, the marker part 510 may follow the tapered surface of the tapered portion 130 and may have a convex shape. In this manner, contact between the inner coil body 200 and the marker part 510 may be suppressed. Thus, stress generated in the tapered portion 130 when the guide wire 2 is bent may be reduced, while the core shaft 100 may be restored more smoothly when the guide wire 2 is restored from the bent state.

As described above, the guide wires 1, 2 have the above-described configurations, which prevents or reduces breakage of the core shaft 100 or deterioration of restorability due to plastic elongation of the wires of the coil body when the guidewires 1, 2 are bent. Without being bound by theory, as described above, the marker parts 500, 510 and the inner coil body 200 can freely move relative to each other along the axial direction of the core shaft 100, so that stress concentration on this region can be avoided. In addition, when the guide wires 1, 2 are bent in a U-shape or the like, the position of the tapered portion 130 in the bent state can be located by the marker parts 500, 510, which allows determination, during operation, whether the above-described bending has developed in the proximal end direction than the above-described tapered portion 130. In this manner, U-shaped bending of the guide wires 1, 2 may be prevented from extending beyond the tapered portion 130 to the large diameter portion 120 and/or the connection portion 140 having a larger outer diameter, and the distal end shape when bent in a U-shape becomes sharp, consequently causing blood vessel perforation. In addition, when the large diameter portion 120 and/or the connection portion 140 are bent in a U-shape, the guide wires 1, 2 cannot be restored to the original substantially straight (unbent) state by the influence of plastic deformation. This deteriorates the operability of the guide wires 1, 2. Therefore, the technician can determine whether the guide wires 1, 2 are excessively bent in a U-shape by confirming the position of the tapered portion 130, and as a result, the procedures can be smoothly continued without deteriorating the operability of the guide wires 1, 2.

Note that the present disclosure is not limited to the configurations of the above-described embodiments, but is defined by the terms of the claims and is intended to include any modifications within the scope and meaning equivalent to the terms of the claims.

Figure 4:
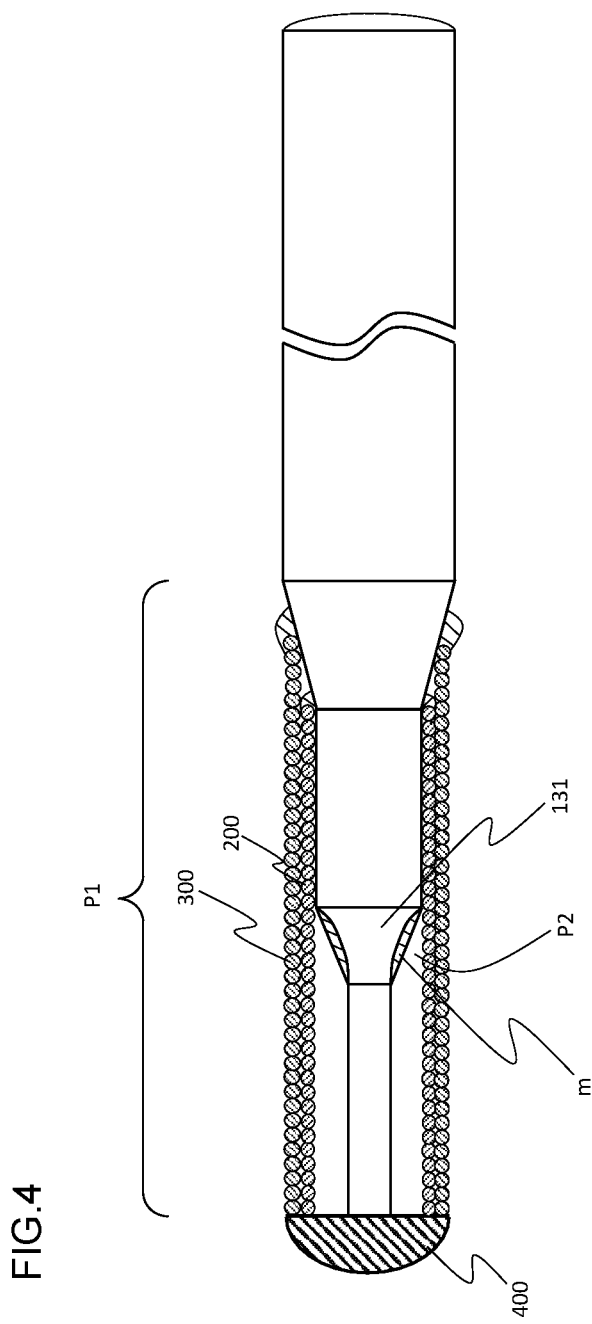
FIG. 4 is a schematic section view illustrating another modification of FIG. 1.

For example, the above-described embodiment has described the guide wires 1, 2 in which the marker parts 500, 510 are provided on the entire outer peripheral surface of the tapered portion 130. Alternatively, the guide wire may include a marker part only provided on a portion of the outer peripheral surface of the tapered portion, a marker part embedded in a concave portion formed on the outer peripheral surface of the tapered portion 130 (for example, see FIG. 4), e.g., the tapered portion may have an arcuate slope rather than a linear slope, a marker part may have a uniform thickness on the tapered portion, a marker part that is discontinuous on the outer peripheral surface of the tapered portion, either radially or laterally, or the like.

Further, the above-described embodiment has described the guide wires 1, 2 having a double coil structure of the inner coil body 200 and the outer coil body 300. However, the guide wire may have a triple or quadruple or more coil structure.

Further, the above-described embodiment has described the guide wires 1, 2 in which each of the inner coil body 200 and the outer coil body 300 is formed using one single wire. However, the guide wire may include the inner coil body and/or the outer coil body that are wound in multiple spirals (multiple turns) using two or more wires, wound using a twisted wire (a bundle of wires in which multiple wires are preliminary twisted mutually) instead of the above-described single wire, or wound in multiple spirals using a plurality of the above-described twisted wires.

Further, the above-described embodiment has exemplified the guide wires 1, 2 including the connection portion 140 between the large diameter portion 120 and the core shaft main body 150 of the core shaft 100. However, the guide wire may be formed such that the large diameter portion is a part of the core shaft main body (a guide wire in which the large diameter portion and the core shaft main body have the same diameter and are continuous with each other).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Obviously, numerous modifications and variations of the present invention are possible in light of the above teachings. It is therefore to be understood that within the scope of the appended claims, the invention may be practiced otherwise than as specifically described herein.

The invention claimed is:

1. A guide wire, comprising:
a core shaft that includes a distal end portion having a decreasing diameter toward a distal end direction;
an inner coil body wound to cover at least a part of an outer periphery of the distal end portion having the decreasing diameter;
an outer coil body wound to cover at least an outer periphery of the inner coil body;
a distal end fixing portion that fixes a distal end of the core shaft, a distal end of the inner coil body, and a distal end of the outer coil body to one another, wherein the distal end portion of the core shaft includes:
a cylindrical small diameter portion adjacent the distal end fixing portion,
a cylindrical large diameter portion inside the inner coil body and the outer coil body, the large diameter portion being further in a proximal end direction than the small diameter portion, the large diameter portion having a larger diameter than the small diameter portion, and
a tapered portion between the small diameter portion and the large diameter portion, the tapered portion being continuous with the small diameter portion and the large diameter portion and increases in diameter from the small diameter portion toward the large diameter portion;
a radiopaque marker on an outer peripheral surface of the tapered portion, the radiopaque marker including a radiopaque substance; and
a gap between the radiopaque marker and the inner coil body, the radiopaque substance extends continuously from a distal end of the tapered portion through to a proximal end of the tapered portion, wherein
the radiopaque substance covers an entirety of the tapered portion from the small diameter portion to the large diameter portion, and
a thickness of the radiopaque marker varies continuously along a longitudinal direction of the core shaft.

2. The guide wire according to claim 1, wherein the gap between the inner coil body and the radiopaque marker increases in the distal end direction while the core shaft extends in a straight line.

3. The guide wire according to claim 2, wherein an outer peripheral surface of the radiopaque marker is convexly curved along the longitudinal direction of the core shaft.

4. The guide wire according to claim 1, wherein the gap between the inner coil body and the radiopaque marker is constant.

5. The guide wire according to claim 1, wherein the outer coil body extends further from the distal end fixing portion than the inner coil body.

6. The guide wire according to claim 1, wherein the thickness of the radiopaque marker increases in the distal end direction.

7. The guide wire according to claim 1, wherein a thickness of a distal end portion of the radiopaque marker decreases toward the distal end direction.

8. The guide wire according to claim 7, wherein an outer peripheral surface of the radiopaque marker is curved along the longitudinal direction of the core shaft.

9. The guide wire according to claim 1, wherein the thickness of the radiopaque marker varies linearly along the longitudinal direction of the core shaft.

10. The guide wire according to claim 1, wherein the radiopaque substance covers only the tapered portion.

11. The guide wire according to claim 1, wherein the thickness of the radiopaque marker together with the diameter of the tapered portion has a diameter of the large diameter portion.

12. The guide wire according to claim 1, wherein an outer peripheral surface of the radiopaque marker is curved along the longitudinal direction of the core shaft.

13. The guide wire according to claim 12, wherein the outer peripheral surface of the tapered portion is concavely curved.

14. The guide wire according to claim 12, wherein the radiopaque substance covers only the tapered portion.

15. The guide wire according to claim 12, wherein the gap between the inner coil body and the radiopaque marker increases in the distal end direction while the core shaft extends in a straight line.

16. The guide wire according to claim 1, wherein the thickness of the radiopaque marker together with the diameter of the tapered portion has a linear slope between the large diameter portion and the smaller diameter portion.

17. The guide wire according to claim 16, wherein the outer peripheral surface of the tapered portion is concavely curved.

* * * * *